United States Patent [19]

Casciani

[11] Patent Number: 4,766,153

[45] Date of Patent: Aug. 23, 1988

[54] ALKYL POLYOXYALKYLENE CARBOXYLATE ESTERS AND SKIN CARE COMPOSITIONS CONTAINING THE SAME

[75] Inventor: Robert V. Casciani, Matthews, N.C.

[73] Assignee: Sandoz Ltd., Basel, Switzerland

[21] Appl. No.: 34,119

[22] Filed: Apr. 1, 1987

Related U.S. Application Data

[63] Continuation-in-part of Ser. No. 857,683, Apr. 30, 1986, abandoned.

[51] Int. Cl.$^4$ .................. A61K 7/48; C07C 69/708
[52] U.S. Cl. .................. 514/785; 252/174.21; 252/174.22; 252/315.4; 252/356; 560/186; 562/587
[58] Field of Search .................. 560/186; 252/174.21, 252/174.22, 315.4, 356; 514/785; 562/587

[56] References Cited

U.S. PATENT DOCUMENTS

| | | | |
|---|---|---|---|
| 2,109,947 | 3/1938 | North | 560/186 |
| 2,417,299 | 3/1947 | Freedman et al. | 514/725 |
| 2,786,013 | 3/1957 | Behrens | 514/756 |
| 2,803,646 | 8/1957 | Bell et al. | 560/186 |
| 2,939,880 | 6/1960 | Montagna et al. | 560/180 |
| 3,060,096 | 10/1962 | Wei | 514/784 |
| 3,127,311 | 3/1964 | Telle et al. | 514/784 |
| 3,489,690 | 1/1970 | Lachampt et al. | 252/308 |
| 3,776,857 | 12/1973 | Lindner | 252/308 |
| 4,163,114 | 7/1979 | Koleske et al. | 560/186 |
| 4,370,319 | 1/1983 | Chapin et al. | 514/785 |
| 4,416,868 | 11/1983 | Vanlerberghe et al. | 424/59 |
| 4,529,605 | 7/1985 | Lynch et al. | 514/552 |

*Primary Examiner*—Werren B. Lone
*Assistant Examiner*—Vera C. Clarke
*Attorney, Agent, or Firm*—Gerald D. Sharkin; Robert S. Honor; Joseph J. Borovian

[57] ABSTRACT

The invention relates to novel alkyl polyoxyalkylene carboxylate esters and to their use as surface active agents. The novel esters are especially useful as emollients in skin care compositions.

18 Claims, No Drawings

ALKYL POLYOXYALKYLENE CARBOXYLATE ESTERS AND SKIN CARE COMPOSITIONS CONTAINING THE SAME

This application is a continuation-in-part of U.S. patent application Ser. No. 857,683, filed Apr. 30, 1986, now abandoned.

This invention relates to a new class of surface active agents. More particularly, it relates to novel, alkyl polyoxyalkylene carboxylate esters and to their use as surface active agents and, more especially, to their use as emollients in skin care compositions.

Consumers have long desired a moisturizing and conditioning preparation in the form of a hand and body lotion or cream which, when applied, provides cosmetically acceptable tactile properties. A satisfactory skin care composition having superior moisturizing and conditioning properties with cosmetically acceptable tactile properties should exhibit satisfactory feel, lubricity and absorption when applied to the skin. In particular, the composition should exhibit good consistency, should apply evenly to the skin, should be absorbed rapidly and should dry quickly. After application, the skin should feel smooth and clean. The composition should assist in relieving the tight feeling of dry skin and should soothe irritated skin.

Recently, attempts have been made to improve skin care compositions with the introduction of such products as Wondra, Vaseline Intensive Care Lotion and Sensuously Silky. However, these products exhibit various deficiencies. For example, they provide a film which is palpably oily and greasy to the touch upon application. Moreover, the applied films tend to be removed by water without much resistance and do not provide a level of moisturizing which is deemed cosmetically acceptable to consumers.

Accordingly, it is an object of the present invention to provide a new class of surface active agents. It is another object of the present invention to provide a new class of surface active agents which may be employed as the essential emollient component in skin care compositions. It is still another object of the present invention to provide a new class of emollient esters which may be employed as the essential emollient component in skin care compositions, wherein said compositions exhibit moisturizing and conditioning properties. It is yet still another object of the present invention to provide a new class of emollient esters which may be employed as the essential emollient component in skin care compositions, wherein said compositions not only exhibit moisturizing and conditioning properties but cosmetically acceptable tactile properties as well.

The attainment of the above-objects is made possible by a novel class of alkyl polyoxyalkylene carboxylate esters and mixtures thereof having the following formula:

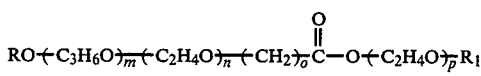

where
R is $C_8$–$C_{22}$ straight or branched chain alkyl;
$R_1$ is $C_1$–$C_{22}$ straight or branched chain alkyl;
m is O or an integer 1 to 4;
n is an integer 3 to 20;
o is an integer 1 to 4; and
p is O or an integer 1 to 20, with the provisos that: 1) when $R_1$ is $C_1$–$C_3$-alkyl, then p is O; and 2) when m is O, n is an integer 6 to 20.

R is preferably $C_{10}$–$C_{18}$ straight or branched chain alkyl, more preferably $C_{10}$–$C_{16}$ straight or branched chain alkyl.

$R_1$, when p is an integer, is preferably $C_6$–$C_{18}$ straight or branched chain alkyl, more preferably $C_{10}$–$C_{16}$ straight or branched chain alkyl.

$R_1$, when p is O, is preferably $C_3$–$C_{18}$ straight or branched chain alkyl.

The variable n, when m is O, is preferably 6 to 18, more preferably 6 to 14.

The variable n, when m is an integer, is preferably 3 to 12, most preferably 3 to 10.

The variable o is preferably 1 to 3, more preferably 1 or 2.

The variable p is preferably O or an integer 1 to 16, more preferably O or an integer 1 to 12.

The variables m, n, o and p are average values. As is clearly evident, the variables m, n, o and p must be whole numbers in the individual compounds of this invention.

Preferred compounds and mixtures are those of formula Ia:

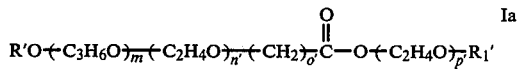

where
R' is $C_{10}$–$C_{18}$ straight or branched chain alkyl;
$R_1'$, when p' is O, is $C_3$–$C_{18}$-straight or branched chain alkyl or, when p' is an integer, is $C_6$–$C_{18}$-straight or branched chain alkyl;
m is as defined above;
n', when m is O, is an integer 6 to 18 or, when m is other than O, is an integer 3 to 12;
o' is an integer 1 to 3; and
p' is O or an integer 1 to 16.

The more preferred compounds and mixtures are those of formula Ib:

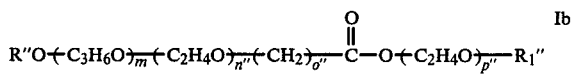

where
R" is $C_{10}$–$C_{16}$ straight or branched chain alkyl;
$R_1"$, when p" is O, is $C_3$–$C_{18}$-straight or branched chain alkyl and, when p" is an integer, is $C_{10}$–$C_{16}$-straight or branched chain alkyl;
m is as defined above;
n", when m is O, is an integer 6 to 14 or, when m is other than O, is an integer 3 to 10;
o" is an integer 1 or 2; and
p" is O or an integer 1 to 12.

The even more preferred compounds and mixtures are those of formula Ic:

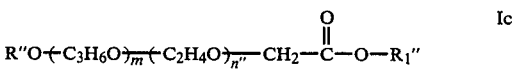

where
$R_1"$ is $C_3$–$C_{18}$ straight or branched chain alkyl; and
R", m and n" are as defined above.

Suitable alcohol precursors of the alkyl, polyoxyalkylene carboxylate esters of this invention are straight or branched chain primary alcohols having from 8 to 22 carbon atoms. Typical examples of alcohols having a straight chain configuration are n-octyl, n-nonyl, n-decyl, n-undecyl, n-dodecyl, n-tridecyl, n-tetradecyl, etc., whereas isodecyl and isostearyl are exemplary of alcohols having a branched chain configuration. A mixture of alcohols may be used and this is generally true when using commercial alcohols which are often available as a blend of several alcohols. Specific examples are a mixture of $C_{12}$-$C_{15}$ straight chain alcohols available commercially from Union Carbide; a mixture of $C_{12}$-$C_{15}$ predominantly straight chain alcohols containing approximately 20% branching available commercially from Shell Chemical Co.; and a mixture of alcohols, at least 70 mol % of which is branched 1-decanols available commercially from Exxon Chemical Co. When employing a mixture of alcohols, the number of carbon atoms in the alcohol is referred to as an average number and such number can be determined by vapor phase chromatography and the hydroxyl number.

The compounds and mixtures of formula I are produced by more or less conventional methods. Thus, the alkyl polyoxyalkylene carboxylate esters of this invention may be prepared by carboxyalkylating the adduct resulting from the propoxylation and/or ethoxylation of a straight or branched chain primary alcohol having from 8 to 22 carbon atoms and then esterifying the carboxyalkylated acid resulting therefrom with a straight or branched chain primary alcohol optionally containing one or more ethylene oxide groups.

More particularly, a catalytic amount, e.g., from about 0.2% to 1%, preferably 0.3% to 0.75%, by weight of the total amount of reactants, including the respective alkylene oxides, of an alkaline catalyst is added to the alcohol, or mixture thereof, to be alkoxylated.

Catalysts which may be employed include alkali metal hydroxides, sodium ethoxide, sodium methoxide, alkali metal acetates and dimethylamine, and mixtures thereof. Preferred catalysts are the alkali metal hydroxides, more preferably sodium hydroxide and potassium hydroxide. Other types of catalysts commonly used for alkylene oxide condensation reactions may also be employed.

Optionally, a small amount of a reducing agent may be added to the alcohol or mixture thereof, to be alkoxylated to minimize discoloration of the resulting polyalkoxylated alcohol. Suitable reducing agents which may be employed include sodium borohydride, lithium aluminum hydride, diborane and the like, preferably sodium borohydride.

In preparing a polyoxyalkylated alcohol wherein the polyoxyalkylene chain contains a propylene oxide first block and an ethylene oxide second block, an amount of propylene oxide calculated to provide the desired degree of propoxylation is then introduced and the resulting mixture is allowed to react until the propylene oxide is consumed, as indicated by a drop in reaction pressure. A similar introduction and reaction of a calculated amount of ethylene oxide serves to provide the second block which completes the alkoxylation. Customarily, the alkoxylated product is finally treated with weak acid, e.g., glacial acetic acid, to neutralize any basic catalyst residues.

It should be understood that each separate alkoxylation procedure serves to introduce a desired average number of alkylene oxide units per alcohol molecule. Thus, for example, the initial treatment of an alcohol mixture with m moles of propylene oxide per mole of alcohol serves to effect the propoxylation of each alcohol moiety with propylene oxide to an average of m propylene oxide moieties per alcohol moiety, although some alcohol moieties will have become combined with more than m propylene oxide moieties and some will have become combined with less than m. In general, the maximum number of propyleneoxy units in a single molecule will not exceed 8 and the number of ethyleneoxy units in a single molecule will not exceed 30. The variation in the number of alkylene oxide moieties is not critical as long as the average for the number of units in each block is within the limits set out for the m and n terms in formula I above, which terms, as average values, are other than whole numbers in some instances.

Each alkoxylation is conducted at an elevated temperature and pressure. Suitable reaction temperatures are from about 120° C. to about 220° C., preferably, 130° C. to 180° C. and, more preferably, 140° C. to 160° C. A suitable reaction pressure is achieved by introducing to the reaction vessel the required amount of propylene oxide or ethylene oxide, each of which has a high vapor pressure at the desired reaction temperature. The pressure serves as a measure of the degree of reaction and each alkoxylation is considered to be complete when the pressure no longer decreases with time.

For best results, it is desirable to carry out the alkoxylation under relatively moisture-free conditions and to avoid side reactions which form water. To dry the reaction vessel and connections, they may be swept out with dry, oxygen-free gas, e.g., nitrogen, before introducing the charge. The catalyst or catalyst mixture should also be dry, or substantially so. The propylene oxide and ethylene oxide should preferably be purified to remove moisture and any impurities which are capable of entering into side reactions which yield water.

The resulting alkyl, polyalkoxide intermediates are then carboxyalkylated by the Williamson synthesis, involving reaction with the appropriate chloro- or bromocarboxylic acid or a salt thereof in the presence of sodium hydroxide or metallic sodium. Such reaction is ordinarily not complete; hence the reaction product often contains minor amounts of uncarboxyalkylated alkyl polyalkoxide. While methods are available for separating the uncarboxyalkylated material as well as for assuring essentially complete carboxyalkylation, they are usually tedious and expensive. Fortunately, it has been found that minor proportions of such uncarboxyalkylated material are not particularly harmful, and may even be advantageous.

Carboxyalkylation can also be achieved by oxidation of the alkyl, polyalkoxide intermediate; however, reaction with the appropriate chloro- or bromocarboxylic acid or a salt thereof in the presence of sodium hydroxide or metallic sodium is preferred for completeness. Preferably, the carboxyalkyl group is a carboxymethyl group.

The alkyl, polyalkoxide carboxylic acid is then esterified by reaction with a straight or branched chain $C_1$-$C_{22}$ primary alcohol optionally containing one or more ethylene oxide groups at a mole ratio of alcohol to carboxylic acid of from greater than 5:1 to 1:1. Since ester formation is an equilibrium reaction, a catalyst must be used in order to arrive at the equilibrium point as quickly as possible. Typical catalysts include sulfuric acid, hydrogen chloride, p-toluenesulfonic acid and boron trifluoride. To drive the reaction to completion, the equilibrium must be shifted to the ester side. This can be accomplished by removing the water as it is formed with heat and vacuum, by azeotropic distillation with a water immiscible solvent, by azeotropic distillation with a water miscible solvent, or by using a large excess of one of the reactants (usually the alcohol). For example, an alkyl polyalkoxide carboxylic acid dried under vacuum can be dissolved in a molar excess of an anhydrous alcohol which forms a low boiling azeotrope with water. An acidic catalyst is then added to the mixture, and the reaction is allowed to proceed at reflux until the reaction is essentially complete (usually between 2 and 48 hours). The excess alcohol and water are then removed by distillation at atmospheric pressure and the ester is obtained by decantation. Alternatively, an alkyl polyalkoxide carboxylic acid is dried under vacuum at between 40° and 100° C., preferably between 50° C. and 80° C. To the anhydrous carboxylic acid is added an equimolar portion of a high boiling alcohol. An acidic catalyst is then added and the resultant mixture is heated under vacuum. The water is then removed at a temperature between 120° and 200° C., preferably between 140° and 180° C. After the theoretical amount of water is collected, the mixture is cooled, the vacuum is broken with nitrogen and the ester is obtained by decentation.

The most conspicuous property of the compounds of formula I is their great activity at surfaces and interfaces, making them especially useful as surface active agents. The uses to which surface active agents can be put are numerous and well known and, as a result, the possible applications of these new compounds are extremely varied. Thus, the surface active agents of the present invention are suitable as emulsifiers, dispersing agents, lubricants, wetting agents, levelling agents, softening agents and the like in the textile, leather, paper, lacquer, personal care, e.g., toiletries, cosmetics, etc., and rubber industries. For instance, they can be used as wetting, softening or lubricating agents in the treating and refining of textiles; and for converting liquid or solid substances which per se are insoluble in water (such as hydrocarbons, higher alcohols, oils, fats, waxes and resins) into creamy emulsions, clear solutions or fine, stable dispersions.

In addition, the compounds of formula I are valuable emulsifiers for insecticide compositions and agricultural sprays such as DDT, 2,4-D and the like; are valuable for use as additives to petroleum products, hydraulic fluids, lubricating oils, cutting oils and greases; may be employed as coating aids for use in coating compositions comprising a hydrophilic, film-forming colloid; may be employed as tackifiers in the adhesive layer of adhesive tapes in, e.g., the photographic industry; and as foaming agents, emulsifying agents and softening agents in a wide variety of food products.

The alkyl, polyoxyalkylene carboxylate esters of the instant invention are especially useful as the essential emollient component in skin care compositions, e.g., skin creams, lotions, etc. Their incorporation serves to enhance not only the moisturizing and conditioning properties of the skin care compositions but the tactile properties as well. Such skin care compositions will normally contain from about 0.5% to about 15% or an alkyl, polyoxyalkylene carboxylate ester, preferably from about 1% to about 13%, and more preferably from about 1.5% to about 12%. As indicated above, the alkyl polyoxyalkylene carboxylate esters may be employed as the sole emollient thereof, i.e., totally replace the conventional fatty ester emollient such as isopropyl myristate, isopropyl palmitate, etc., which is the more preferred featue of the instant invention, or said carboxylate esters may be employed in combination with conventional fatty ester emollients, i.e., partially replace the latter, thereby reducing the amount of conventional fatty ester emollient that needs to be employed.

The skin care compositions can contain other ingredients commonly found in such type compositions. For example, a fatty alcohol, or a mixture thereof, may be employed to assist in stabilizing the composition and in providing a cosmetically acceptable viscosity. In general, a $C_{14}$ to $C_{22}$ substantially saturated alkanol is employed. Typical examples of suitable fatty alcohols are cetyl alcohol, stearyl alcohol, etc.

Emulsifiers may also be employed and such may be of the cationic type, e.g., quaternary ammonium compounds such as dimethyl distearyl ammonium chloride, amphoteric type such as betaines or sulfobetaines and nonionic type such as polyethylene glycol monostearate.

In order to improve the lubricity of the skin care compositions, a lubricant is generally employed. Such may be a silicone oil such as dimethylpolysiloxane or other conventional polysiloxane or olive oil.

If desired, a humectant may be present in the skin care compositions. It has been postulated that humectants can be entrapped in the interstices of the surface stratum corneum, where they act as a hygroscopic agent, thus increasing the amount of water held in this area. The water is given up by the humectant as required to contribute to the softening of the skin surface. Typical humectants which may be employed include propylene glycol, polyethylene glycol and mixtures thereof.

The amount of water or aqueous vehicle to be included depends upon the desired consistency of the final product. It is possible to vary the amount of water present to formulate, for example, a thick-flowing liquid or lotion, a semi-liquid thick cream, a paste, etc.

The skin care compositions, in general, comprise from about 1.5% to about 10%, preferably from about 2% to about 8.5% of a fatty alcohol or a mixture thereof; from about 1.5% to about 12%, preferably from about 2% to about 10% of an emulsifying agent; and from about 0.75% to about 50%, preferably from about 1% to about 35% of a lubricant.

Other conventional additives typically employed in skin care compositions may be utilized. Fragrance oils, which mask the odor and provide cosmetic appeal, can be employed. Non-toxic and compatible dyes may be utilized to color the compositions, as desired. Preservatives, such as methyl paraben, propyl paraben and formaldehyde may be utilized.

In addition, other ingredients can be employed beneficially to provide skin-care compositions tailored to a specific use. For example, a sun screen additive such as octyl dimethyl para-aminobenzoic acid can be employed. To provide skin protection, a skin protectant such as zinc oxide and the like can be employed. As a medicament, an essential oil such as menthol can be employed.

The skin care compositions are topically applied in a conventional manner. In general, the compositions may be dispensed from a container and then gently applied to the skin. The compositions are rapidly absorbed and leave the skin with a soft and smooth appearance.

The following examples illustrate the preparation of the alkyl, polyoxyalkylene carboxylate esters of this invention.

EXAMPLE 1

Isodecyl-dipropoxy-hexaethoxymethyl carboxylic acid, isopropyl ester

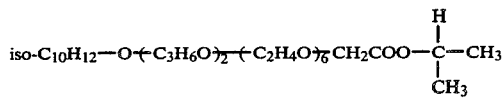

(a) Preparation of dipropoxy-hexaethoxy isodecyl alcohol

To a reaction vessel was added, with stirring, 705.0 g. of decyl alcohol (a mixture of primary, aliphatic alcohols, at least 70 mol% of which is branched 1-decanols, a boiling range of 216° C. to 223° C., a specific gravity @ 20/20° C. of 0.838, a refractive index, $n_D^{20}$, of 1.400, a pour point of $-65°$ F., a viscosity @ 20° C. of 22.5 centistokes and a solubility in water @ 20° C. of $< 0.05$ g./100 g. and available commercially from Exxon Chemical Co.), 10.6 g. of potassium hydroxide (in pellet form) and 0.12 g. of sodium borohydride. After heating the reaction mixture to 60° C. under 30 inches of vacuum (equivalent to 5-10 mm. of mercury), the system was purged with nitrogen to break the vacuum and the purging procedure was repeated two additional times to minimize the presence of air. While maintaining the temperature of the reaction mixture at 60° C. and the vacuum of the reactive system at 30 inches for thirty minutes, a dropping funnel containing 260.0 g. of propylene oxide under vacuum was purged with nitrogen to break the vacuum and the purging procedure was repeated two additional times. The temperature of the reaction mixture was then raised to 100° C., at which time the addition of propylene oxide to the reaction mixture commenced, which effected a lowering of the vacuum of the reaction system to 15 inches. Over a period of sixty minutes, the remaining propylene oxide was added, while the temperature of the resulting reaction mixture slowly rose to 155° C. and the vacuum of the resulting reaction system slowly decreased to 9 inches. After allowing the reaction mixture to react further until the vacuum of the reaction system rose to 30 inches, the procedure described above was repeated with an additional 257.0 g. of propylene oxide, which was added over a period of sixty minutes as the vacuum of the reaction system slowly decreased to 8 inches. After allowing the propoxylated alcohol reaction mixture to react further until the vacuum of the reaction system rose to 30 inches, the procedure described above was repeated with 1178.0 g. of ethylene oxide, which was added over a period of sixty minutes as the vacuum of the reaction system slowly decreased. After allowing the polyalkoxylated alcohol mixture to react further until the vacuum of the reaction system rose to 30 inches, the reaction system was purged with nitrogen to break the vacuum, the temperature of the system was cooled to 85° C. and an additional 0.12 g. of sodium borohydride was added to the polyalkoxylated alcohol mixture. The reaction system was then kept under a nitrogen atmosphere for 2 hours, while the temperature was maintained between 85° and 90° C. After neutralizing the catalyst present with glacial acetic acid, filtering of the insoluble materials yielded a translucent, pale yellow liquid of the formula

(b) Preparation of isodecyl-dipropoxy-hexaethoxymethyl carboxylic acid

To 957.6 g (1.78 moles) of the compound prepared in (a) above, was alternately added, in small portions over a period of 3½ hours at a temperature range of 25°–50° C., 71.2 g. of sodium hydroxide (1.78 moles) and 207.7 g. of sodium monochloroacetate (1.78 moles). Upon completion of the addition, the temperature of the resulting reaction mixture was maintained at 50° C. for 30 minutes, after which time the temperature was raised to 75° C. over a period of 30 minutes. After keeping the reaction mixture at a temperature of 75° C. for 90 minutes, it was cooled to 50° C. and acidified with 175 g. of sulfuric acid (50% conc.) in 600 g. of water, after which time separation of the water-soluble salt yielded an oil of the formula

Preparation of the Title Compound 158.7 g (0.2 moles) of the compound prepared in (b) above was heated to 60° C. under vacuum in a reaction vessel. After 12.7 g of water was collected, the reaction vessel was cooled and the vacuum was broken. 100 g. (1.64 moles) of anhydrous isopropyl alcohol was then added to the reaction vessel, after which time a catalytic amount (25 drops) of 98% sulfuric acid was added to the reaction mixture. The resultant mixture was then heated to reflux temperature and maintained at this temperature for a period of 24 hours. After removing the isopropyl alcohol and water by distillation, decantation yielded the title compound.

EXAMPLE 2

Isodecyl-dipropoxy-hexaethoxymethyl carboxylic acid, cetyl ester

Following essentially the last step of the procedure in preparing the compound of Example 1, and using in place of isopropyl alcohol, an amount of cetyl alcohol equivalent to the amount of carboxylic acid the title compound was obtained by the removal of water under vacuum at elevated temperatures during the reaction.

EXAMPLE 3

Lauryl-hexaethoxymethyl carboxylic acid, cetyl ester

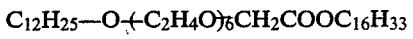

(a) Preparation of hexaethoxy lauryl alcohol

To a reaction vessel vas added, with stirring, 664.7 g (3.57 moles) of lauryl alcohol and 8.5 g of potassium hydroxide (in pellet form). While the reaction mixture was heated to 100° C., the reaction vessel was evacuated to a pressure of 5 mm of mercury and kept under vacuum for thirty minutes, after which time the system was purged with nitrogen to break the vacuum. The temperature of the reaction mixture was then raised to 160° C., at which time the addition of 1059 g (24.08 moles) of ethylene oxide to the reaction mixture was commenced. The temperature of the resulting reaction mixture was kept at a range of from about 160° to about 170° C. throughout the gradual addition of ethylene oxide. Upon completion of the ethylene oxide addition, the reaction mixture was cooled to yield a compound of the formula $$C_{12}H_{25}\!-\!\!(OC_2H_4)_6\!OH$$

(b) Preparation of lauryl-hexaethoxy-methyl carboxylic acid

Following essentially the procedure of Example 1(b), and using in place of the compound prepared in Example 1(a), an approximately equivalent amount of the compound prepared in (a) above, a compound of the formula $$C_{12}H_{25}\!-\!O\!\!-\!(C_2H_4O)_6CH_2COOH$$

was obtained.

Preparation of the tile compound 101.6 g (0.2 moles) of the compound prepared in (b) above was heated to 50° C. under vacuum in a reaction vessel. After 14 ml of water was collected, the reaction vessel was cooled and the vacuum was broken. 48.2 g. (0.2 moles) of cetyl alcohol was then added to the reaction vessel and the mixture was heated until the alcohol completely melted. A catalytic amount ($\sim$5 drops) of 98% sulfuric acid was then added and the resultant mixture was heated to 130° C. under vacuum. After 3 hours, 3.9 mls of water was collected. Since no further generation of water was observed, the mixture was cooled to 5° C., after which time decantation yielded the title compound.

EXAMPLE 4

Lauryl-hexaethoxymethyl carboxylic acid, isopropyl ester $$C_{12}H_{25}\!-\!O\!\!-\!(C_2H_4O)_6CH_2COO\!-\!\underset{\underset{CH_3}{|}}{\overset{\overset{H}{|}}{C}}\!-\!CH_3$$

Following essentially the last step of the procedure in preparing the compound of Example 3, and using in place of cetyl alcohol, an excess amount of isopropyl alcohol, the title compound was obtained by azeotropic distillation of the water of reaction at atmospheric pressure.

EXAMPLE 5

Following essentially the procedure of Example 3(a) and employing the appropriate starting alcohol and the appropriate amount of ethylene oxide, the following compounds are obtained:

(a) $R^a\!-\!(OC_2H_4)_8OH$ where $R^a$ is the residue of a mixture of $C_{12}$-$C_{15}$ predominantly straight chain alcohols containing approximately 20% branching and available commercially from Shell Chemical Co.;

(b) $R^b\!-\!(OC_2H_4)_{12}OH$ where $R^b$ is the residue of a mixture of $C_{12}$-$C_{15}$ straight chain alcohols and available commercially from Union Carbide;

(c) $R^c\!-\!(OC_2H_4)_{11}OH$ where $R^c$ is the residue of a mixture of primary, aliphatic alcohols, at least 70 mol % of which is branched 1-decanols and available commercially from Exxon Chemical Co.;

(d) $R^d\!-\!(OC_2H_4)_{10}OH$ where $R^d$ is the residue of a commercially available isostearyl alcohol containing a mixture of branched methyl isomers; and (e) $C_{16}H_{33}\!-\!(OC_2H_4)_{10}OH$.

EXAMPLE 6

Following essentially the procedure of Example 1(b), and using in place of the compound prepared in Example 1(a), an approximately equivalent amount of compounds 5(a)-5(e), there was obtained:

(a) $R^a\!-\!O\!\!-\!(C_2H_4O)_8CH_2COOH$ where $R^a$ is as defined above;

(b) $R^b\!-\!O\!\!-\!(C_2H_4O)_{12}CH_2COOH$ where $R^b$ is as defined above;

(c) $R^c\!-\!O\!\!-\!(C_2H_4O)_{11}CH_2COOH$ where $R^c$ is as defined above;

(d) $R^d\!-\!O\!\!-\!(C_2H_4O)_{10}CH_2COOH$ where $R^d$ is as defined above; and (e) $C_{16}H_{33}\!-\!O\!\!-\!(C_2H_4O)_{10}CH_2COOH$, respectively.

EXAMPLE 7

(a) Following essentially the last step of the procedure in preparing the compound of Example 3, and using in place of the compound prepared in Example 3(b), an approximately equivalent amount of the compound of Example 6(a), a compound of the formula $$R^a\!-\!O\!\!-\!(C_2H_4O)_8CH_2COOC_{16}H_{33}$$

was obtained, where $R^a$ is as defined above.

(b) Following essentially the last step of the procedure in preparing the compound of Example 3, and using in place of the compound prepared in Example 3(b), an approximately equivalent amount of the compound of Example 6(a), and using in place of the cetyl alcohol, an excess amount of isopropyl alcohol, a compound of the formula $$R^a\!-\!O\!\!-\!(C_2H_4O)_8CH_2COO\!-\!\underset{\underset{CH_3}{|}}{\overset{\overset{H}{|}}{C}}\!-\!CH_3$$

was obtained, where $R^a$ is as defined above.

EXAMPLE 8

(a) Following essentially the last step of the procedure in preparing the compound of Example 3, and using in place of the compound prepared in Example 3(b), an approximately equivalent amount of the compound of Example 6(b), a compound of the formula $$R^b\!-\!O\!\!-\!(C_2H_4O)_{12}CH_2COOC_{16}H_{33}$$

was obtained, where $R_b$ is as defined above.

(b) Following essentially the last step of the procedure in preparing the compound of Example 3, and using in place of the compound prepared in Example 3(b), an approximately equivalent amount of the compound of Example 6(b), and using in place of the cetyl alcohol, an excess amount of isopropyl alcohol, a compound of the formula

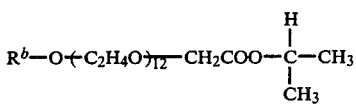

was obtained, where $R^b$ is as defined above.

EXAMPLE 9

(a) Following essentially the last step of the procedure in preparing the compound of Example 3, and using in place of the compound prepared in Example 3(b), an approximately equivalent amount of the compound of Example 6(c), a compound of the formula

was obtained, where $R^c$ is as defined above.

(b) Following essentially the last step of the procedure in preparing the compound of Example 3, and using in place of the compound prepared in Example 3(b), an approximately equivalent amount of the compound of Example 6(c), and using in place of the cetyl alcohol, an excess amount of isopropyl alcohol, a compound of the formula

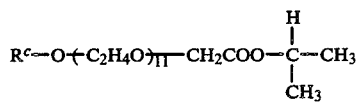

was obtained, where $R^c$ is as defined above.

EXAMPLE 10

(a) Following essentially the last step of the procedure in preparing the compound of Example 3, and using in place of the compound prepared in Example 3(b), an approximately equivalent amount of compound of Example 6(d), a compound of the formula

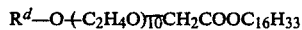

was obtained, where $R^d$ is as defined above.

(b) Following essentially the last step of the procedure in preparing the compound of Example 3, and using in place of the compound prepared in Example 3(b), an approximately equivalent amount of the compound of Example 6(d), and using in place of the cetyl alcohol, an excess amount of isopropyl alcohol, a compound of the formula

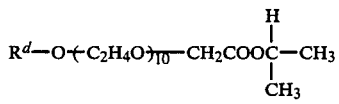

was obtained, where $R_d$ is as defined above.

EXAMPLE 11

(a) Following essentially the last step of the procedure in preparing the compound of Example 3, and using in place of the compound prepared in Example 3(b), an approximately equivalent amount of the compound of Example 6(e), a compound of the formula

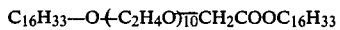

was obtained.

(b) Following essentially the last step of the procedure in preparing the compound of Example 3, and using in place of the compound prepared in Example 3(b), an approximately equivalent amount of the compound of Example 6(e), and using in place of the cetyl alcohol, an excess amount of isopropyl alcohol, a compound of the formula

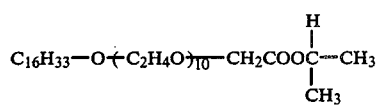

was obtained.

It should be understood that in all of the examples above, the indicated number of propyleneoxy units and ethyleneoxy units are average values.

EXAMPLE 12

To demonstrate the desired emollient properties of the alkyl polyoxyalkylene carboxylate esters of this invention, a number of essentially identical body cream formulations were prepared, one of which contains a conventional fatty ester as the emollient component, i.e., isopropyl myristate, and the remaining formulations containing a representative number of carboxylate esters embraced by this invention as the emollient component. The formulations are as follows:

| Ingredients | Weight Percent | | | | |
|---|---|---|---|---|---|
| | A | B | C | D | E |
| cetyl alcohol | 2.5 | 2.5 | 2.5 | 2.5 | 2.5 |
| stearyl alcohol | 5.0 | 5.0 | 5.0 | 5.0 | 5.0 |
| isopropyl myristate | 2.0 | — | — | — | — |
| light silicone oil | 1.0 | 1.0 | 1.0 | 1.0 | 1.0 |
| Pationic SSL ® (amphoteric emulsifier) | 1.5 | 1.5 | 1.5 | 1.5 | 1.5 |
| water | 82.6 | 82.6 | 82.6 | 82.6 | 82.6 |
| propylene glycol | 5.0 | 5.0 | 5.0 | 5.0 | 5.0 |
| Example 8b | — | 2.0 | — | — | — |
| Example 9b | — | — | 2.0 | — | — |
| Example 10b | — | — | — | 2.0 | — |
| Example 1 | — | — | — | — | 2.0 |

The above formulations were prepared by heating the water to 70° C., heating the remaining ingredients to 70° C., and after adding the water slowly, with stirring, to the heated mixture of ingredients, allowing the resultant mixture to cool to room temperature.

A panel of twenty people was then instructed to apply formulation A to his or her skin and to assess the emolliency imparted against each of formulations B through E by selecting the formulation which, in their opinion, provides a greater degree of emolliency. The results of the individual comparisons are as follows, with a spread of 10% or less considered no difference or equal performance:

| A | B | C | D | E | No difference |
|---|---|---|---|---|---|
| 50% | 40% | — | — | — | 10% |
| 40% | — | 55% | — | — | 5% |
| 50% | — | — | 40% | — | 10% |
| 30% | — | — | — | 50% | 20% |

EXAMPLE 13

To again demonstrate the desired emollient properties of the alkyl polyoxyalkylene carboxylate esters of this invention, a number of essentially identical nonionic-based, oil-in water body lotion formulations were prepared, one of which contains a conventional fatty ester as the emollient component, i.e., polyethylene glycol (400) distearate, and the remaining formulations containing a representative number of carboxylate esters embraced by this invention as the emollient component. The formulations are as follows:

| Ingredients | Weight percent | | | | |
|---|---|---|---|---|---|
| | A | B | C | D | E |
| A. polyethylene glycol (400) monostearate | 2.5 | 2.5 | 2.5 | 2.5 | 2.5 |
| polyethylene glycol (400) distearate | 2.5 | — | — | — | — |
| olive oil | 47.5 | 47.5 | 47.5 | 47.5 | 47.5 |
| propyl paraben | 0.15 | 0.15 | 0.15 | 0.15 | 0.15 |
| Example 8a | — | 2.5 | — | — | — |
| Example 9a | — | — | 2.5 | — | — |
| Example 10a | — | — | — | 2.5 | — |
| Example 2 | — | — | — | — | 2.5 |
| B. methyl paraben | 0.15 | 0.15 | 0.15 | 0.15 | 0.15 |
| water | 46.8 | 46.8 | 46.8 | 46.8 | 46.8 |

The above formulations were prepared by combining and heating the components of A to 70° C., combining and heating the components of B to 70° C., and after adding A to B, with stirring, allowing the resultant mixture to cool to room temperature.

A panel of twenty people was then instructed to apply formulation A to his or her skin and to assess the emolliency imparted against each of formulations B through E by selecting the formulation which, in their opinion, provides a greater degree of emolliency. The results of the individual comparisons are as follows, with a spread of 10% or less considered no difference or equal performance:

| A | B | C | D | E | No difference |
|---|---|---|---|---|---|
| 25% | 75% | — | — | — | — |
| 45% | — | 55% | — | — | — |
| 70% | — | — | 30% | — | — |
| 45% | — | — | — | 55% | — |

EXAMPLE 14

To further demonstrate the desired emollient properties of the alkyl polyoxyalkylene carboxylate esters of this invention, a number of additional essentially identical oil-in-water body lotion formulations were prepared, one of which contains a conventional fatty ester as the emollient component, i.e., isopropyl palmitate, and the remaining formulations containing a representative number of carboxylate esters embraced by this invention as the emollient component. The formulations are as follows:

| Ingredients | Weight percent | | | |
|---|---|---|---|---|
| | A | B | C | D |
| A. isopropyl palmitate | 10 | — | — | — |
| Arlacel 60 (non-ionic emulsifier) | 2 | 2 | 2 | 2 |
| Tween 60 (polysorbate) | 3 | 3 | 3 | 3 |
| Example 8b | — | 10 | — | — |
| Example 9b | — | — | 10 | — |
| Example 1 | — | — | — | 10 |
| B. water | 85 | 85 | 85 | 85 |

The above formulations were prepared by combining and heating the components of A to 70° C., heating the water to 72° C., and after adding the water slowly, with stirring, to the heated mixture of ingredients, allowing the resultant mixture to cool to room temperature.

A panel of twenty people was then instructed to apply formulation A to his or her skin and to assess the emolliency imparted against each of the formulations B through D by selecting the formulation which, in their opinion, provides a greater degree of emolliency. The results of the individual comparisons are as follows, with a spread of 10% or less considered no difference or equal performances:

| A | B | C | D | No difference |
|---|---|---|---|---|
| 30% | 70% | — | — | — |
| 25% | — | 60% | — | 15% |
| 35% | — | — | 55% | 10% |

What is claimed is:

1. A compound of formula I,

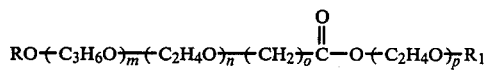

where
R is $C_8$–$C_{22}$ straight or branched chain alkyl;
$R_1$ is $C_1$–$C_{22}$ straight or branched chain alkyl;
m is O or an integer 1 to 4;
n is an integer 3 to 20;
o is an integer 1 to 4; and
p is O or an integer 1 to 20, with the provisos that: (1) when $R_1$ is $C_1$–$C_3$ alkyl, then p is O; and (2) when m is O, n is an integer 6 to 20,
or a mixture of said compounds.

2. A compound according to claim 1 of formula Ia,

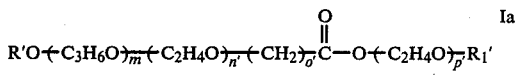

where
R' is $C_{10}$–$C_{18}$ straight or branched chain alkyl;
$R_1'$, when p' is O, is $C_3$–$C_{18}$-straight or branched chain alkyl or, when p' is an integer, is $C_6$–$C_{18}$-straight or branched chain alkyl;
m is as defined in claim 1;
n', when m is O, is an integer 6 to 18 or, when m is other than O, is an integer 3 to 12;
o' is an integer 1 to 3; and
p' is O or an integer 1 to 16,
or a mixture of said compounds.

3. A compound according to claim 2 of formula Ib,

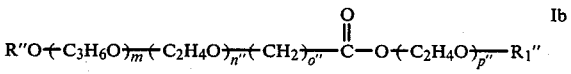

where
R″ is $C_{10}$–$C_{16}$ straight or branched chain alkyl;
$R_1″$, when p″ is O, is $C_3$–$C_{18}$-straight or branched chain alkyl or, when p″ is an integer, is $C_{10}$–$C_{16}$-straight or branched chain alkyl;
m is as defined in claim 2;
n″, when m is O, is an integer 6 to 14 or, when m is other than O, is an integer 3 to 10;
o″ is an integer 1 or 2; and
p″ is O or an integer 1 to 12,
or a mixture of said compounds.

4. A compound according to claim 3 of formula Ic:

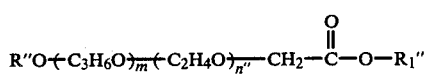

where
$R_1″$ is $C_3$–$C_{18}$ straight or branched chain alkyl; and
R″, m and n″ are as defined in claim 3, or a mixture of said compounds.

5. A mixture of compounds according to claim 4 having the formula

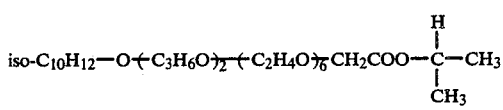

6. A mixture of compounds according to claim 4 having the formula

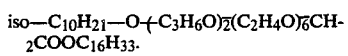

7. mixture of compounds according to claim 4 having the formula

where $R^a$ is the residue of a mixture of $C_{12}$–$C_{15}$ predominantly straight chain alcohols containing approximately 20% branching.

8. A mixture of compounds according to claim 4 having the formula

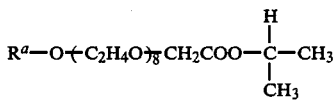

where $R^a$ is the residue of a mixture of $C_{12}$–$C_{15}$ predominantly straight chain alcohols containing approximately 20% branching.

9. A mixture of compounds according to claim 4 having the formula

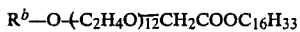

where $R^b$ is the residue of a mixture of $C_{12}$–$C_{15}$ straight chain alcohols.

10. A mixture of compounds according to claim 4 having the formula

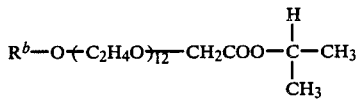

where $R^b$ is the residue of a mixture of $C_{12}$–$C_{15}$ straight chain alochols.

11. A mixture of compounds according to claim 4 havig the formula

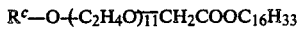

where $R_c$ is the residue of a mixture of primary, aliphatic alcohols, at least 70 mol % of which is branched 1-decanols.

12. A mixture of compounds according to claim 4 having the formula

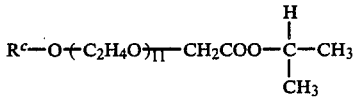

where $R^c$ is the residue of a mixture of primary aliphatic alcohols, at least 70 mol % of which is branched 1-decanols.

13. A skin care composition for moisturizing and conditioning the skin comprising, as the essential emollient component, from about 0.5% to about 15% of a compound according to claim 1, or a mixture thereof, and a carrier therefor.

14. A composition according to claim 13 wherein the essential emollient component is present in an amount of from about 1% to about 13%.

15. A composition according to claim 14 wherein the essential emollient component is present in an amount of from about 1.5% to about 12%.

16. A compound of formula Id:

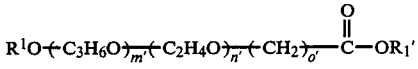

where
R′ is $C_{10}$–$C_{18}$ straight or branched chain alkyl;
$R_1′$ is $C_3$–$C_{18}$ straight or branched chain alkyl;
m′ is an integer 1 to 4;
n′ is an integer 3 to 12; and
o′ is an integer 1 to 3;
or a mixture of said compounds.

17. A compound according to claim 16 of formula Id′:

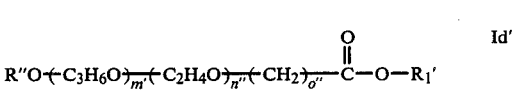

where
R″ is $C_{10}$–$C_{16}$ straight or branched chain alkyl;
n″ is an integer 3 to 10;
o″ is an integer 1 or 2;
and $R_1′$ and m′ are as defined in claim 16, or a mixture of said compounds.

18. A compound according to claim 17 of formula Id″:

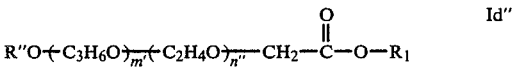

where R″, $R_1′$, m′ and n″ are as defined in claim 17, or a mixture of said compounds.

* * * * *